United States Patent [19]

Hare et al.

[11] Patent Number: 4,867,680
[45] Date of Patent: Sep. 19, 1989

[54] PRE-LOADED DENTAL IMPRESSION PACKAGE AND METHOD OF MAKING

[75] Inventors: Pamela H. Hare; Robert V. Hare, both of Georgetown; Paul D. Hammesfahr, Dover, all of Del.

[73] Assignee: Dentsply Research & Development Corp., Milford, Del.

[21] Appl. No.: 32,903

[22] Filed: Mar. 31, 1987

[51] Int. Cl.$^4$ .............................................. A61C 9/00
[52] U.S. Cl. ........................................ 433/37; 433/71
[58] Field of Search ..................... 206/63.5; 433/37, 71

[56] References Cited

U.S. PATENT DOCUMENTS

| | | | |
|---|---|---|---|
| 2,178,663 | 11/1939 | Harrison | 206/63.5 |
| 3,064,354 | 11/1962 | Pos | 433/71 |
| 3,882,601 | 5/1975 | Jahn . | |
| 4,227,877 | 10/1980 | Tureaud et al. | 433/37 |
| 4,267,133 | 5/1981 | Kohmura et al. . | |
| 4,375,966 | 3/1983 | Freeman | 433/73 |
| 4,411,625 | 10/1983 | Koblitz et al. . | |
| 4,445,856 | 5/1984 | Sturtzkopf | 433/71 |
| 4,468,202 | 8/1984 | Cohen . | |
| 4,521,193 | 6/1985 | Cialone . | |
| 4,543,063 | 9/1985 | Cohen . | |
| 4,544,359 | 10/1985 | Waknine . | |
| 4,544,467 | 10/1985 | Bunker et al. . | |
| 4,553,936 | 11/1985 | Wang . | |
| 4,624,640 | 11/1986 | Tesini | 433/71 |

Primary Examiner—Nancy A. B. Swisher
Attorney, Agent, or Firm—David E. Wheeler; Edward J. Hanson, Jr.

[57] ABSTRACT

A dental impression package pre-loaded with dental impression material adapted for taking accurate impressions of a patient's teeth and/or gums by professional personnel is provided. The impression material used is flowable to a desired degree and has a viscosity of substantially one million centipoises. Packaging a pre-loaded dental impression tray is accomplished by first quickly immersing the loaded tray in a solution of natural latex for a few seconds and then quickly removing the coated product followed by quickly immersing it in a coagulating solution of acetic acid for a few seconds to stabilize the latex coating; withdrawing the stabilized coated product; drying it; and suitably packaging the product for storage and sale. If the impression material is of a light-curable nature, the packaging is of light-opaque nature.

21 Claims, 1 Drawing Sheet

PRE-LOADED DENTAL IMPRESSION PACKAGE AND METHOD OF MAKING

BACKGROUND OF THE INVENTION

The making of dental impressions is a precise art because of the necessity of forming a mold in which an accurate model of dental anatomy may be made. Heretofore, it has been customary for many years to mix the material in which the impression is to be made from certain ingredients and then disposing the same in a conventional impression tray of various types. It is obvious that if the material in which the impression is to be made is relatively readily flowable, it is capable of entering fissures and interstices, whereby, when the mold material is introduced into the molded cavity of the impression, it will be capable of reproducing the minute as well as the major features of the dental anatomy. Obviously; however, the more viscous the impression material, the less likelihood there is of small details of the anatomy being reproduced in the mold of which the pattern is to be made.

Examples of previous techniques in the use of dental impression material in an impression tray or otherwise, heretofore, are found in the prior art U.S. Pat. No. 3,390,458 to Lytton dated July 2, 1968, represents a special type of device for making dental impressions particularly capable of pressing the surrounding gum away from a tooth around the gingival, whereby the pattern molded from the impression will extend below the gum line.

Another example of the use of a conventional tray is the subject matter of U.S. Pat. No. 3,552,601 to Jahn dated May 13, 1975. In this patent, there is provided a spacer hood which is stretched over the impression material and the impression tray is inserted into the mouth of a patient and the patient is asked to close his mouth in biting on the impression material. To form a more precise impression, the spacer hood then is removed, a secondary impression material is applied and the impression tray again is introduced into the mouth of the patient so that a second impression may be taken.

A more recent development in the production of loaded dental impression trays which are pre-filled with impression material comprises the subject matter of U.S. Pat. No. 4,553,936 to Wang dated Nov. 19, 1985, and assigned to the assignee of the present invention. In this disclosure a transparent impression tray is provided which is filled with a light-curable impression material. When thus filled, the impression material is covered with a light-opaque covering which extends across the top and ends of the tray and the exterior surfaces of the tray are covered with light-opaque material such as metal foil; the foil serving an additional advantage of reflecting actinic light which is applied to the transparent tray and thus causes the light to permeate the entire mass of the impression material when such artificial light is applied thereto.

The prior art methods of using dental impression materials are cumbersome to use in the dental operatory or laboratory because many of the prior art materials are cured using two-component self-cured systems, and must therefore be prepared in the operatory or laboratory immediately prior to use. It is difficult for the practitioner to keep air voids out of the material when it is mixed; and after the preparation has begun, he has a limited time, usually about 5 minutes, in which to use the material before it self cures or begins to cure. Consequently, batches of dental impression materials made in the operatory and laboratory sometimes have to be discarded and the procedures repeated Also, it is sometimes difficult for the practitioner to judge the correct amount of material to be used to obtain an impression, and excess material has a tendency to escape from the tray and become loose in the mouth, and said loose material may cause the patient discomfort and trigger the gagging reflex. When flowable impression materials are used, the tendency of the material to flow out of a dental tray may cause similar problems.

Accordingly, there is a need in the art for means and a method for obtaining dental impressions whereby the practitioners time in the operatory is reduced, there is less mess involved, the amounts of impression material to be used are premeasured, the dental impression material to be used is free of air voids, where means are provided to prevent dental impression material from flowing out of a tray, and provides for increased patient comfort It has been found that the above objectives can be obtained by using a light activated, prepackaged, premeasured impression material

SUMMARY OF THE INVENTION

The present invention provides a process for prepackaging a flowable dental impression material comprising the steps of predisposing the dental impression material in a shape suitable for obtaining a dental impression, and retaining at least a portion of said dental impression material in said shape by encasing the dental impression material in a skin which has strength and stretch resistance which is suitable for retaining said shape. The skin is provided in a substantially continuous layer over the impression material. The impression material alone may be provided in a shape suitable for taking impressions, or the impression material may be loaded into a dental tray and the tray as well as the impression material may be encased in said skin. The dental impression material may be light activated and accordingly may be further contained in an opaque outer package.

A prepackaged dental impression material is also provided. The prepackaged dental impression material of the invention comprises dental impression material and a substantially continuous skin overlying the dental impression material. The skin comprises either a flexible, deformable and stretch resistant material or a rigid, easily punctured material. The impression material may be provided in a cylindrical U-shape or may be preloaded in a dental impression tray. The package may also be provided with an additional opaque wrapper enclosing the dental impression material and the skin.

The method of the invention, and the prepackaged dental impression material of the invention provide means for reducing the practitioner's time in the operatory, and substantially eliminates the mess and resulting waste of impression material encountered when it is required to prepare the impression material in the operatory or laboratory. A premeasured impression material, free of air voids, and a means of preventing impression material from becoming loose in the patient's mouth are provided, thereby increasing patient comfort. The impression material is contained, thereby making it possible to use a more flowable material, and the material is cured while in contact with the dental anatomy, making it possible to obtain a very detailed dental impression.

Details of the foregoing objects and of the invention, as well as other objects thereof, are set forth in the following specification and illustrated in the accompanying drawings, comprising a part thereof.

DETAILED DESCRIPTION OF THE PREFERRED EMBODIMENTS OF THE INVENTION

Figure 1:
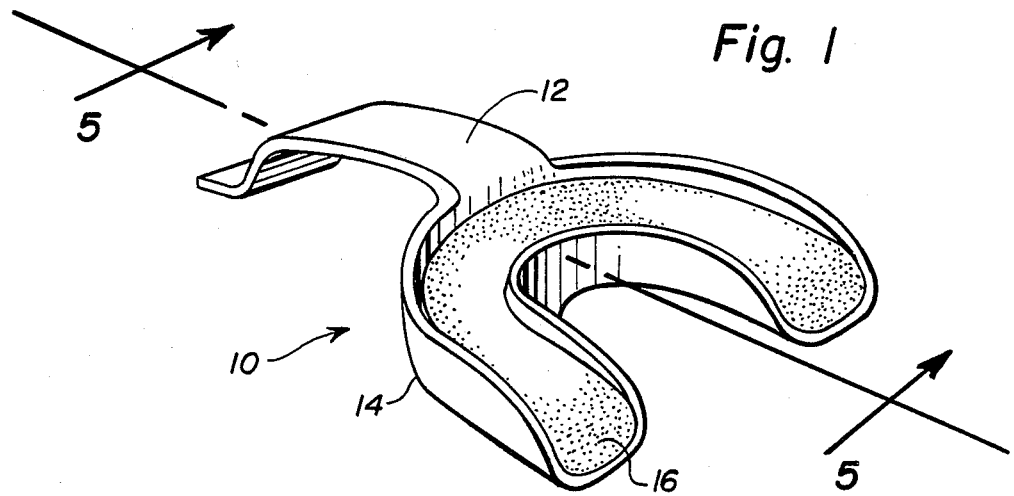
FIG. 1 is a perspective view showing an impression tray loaded with impression material.
Figures 2, 3, 4:
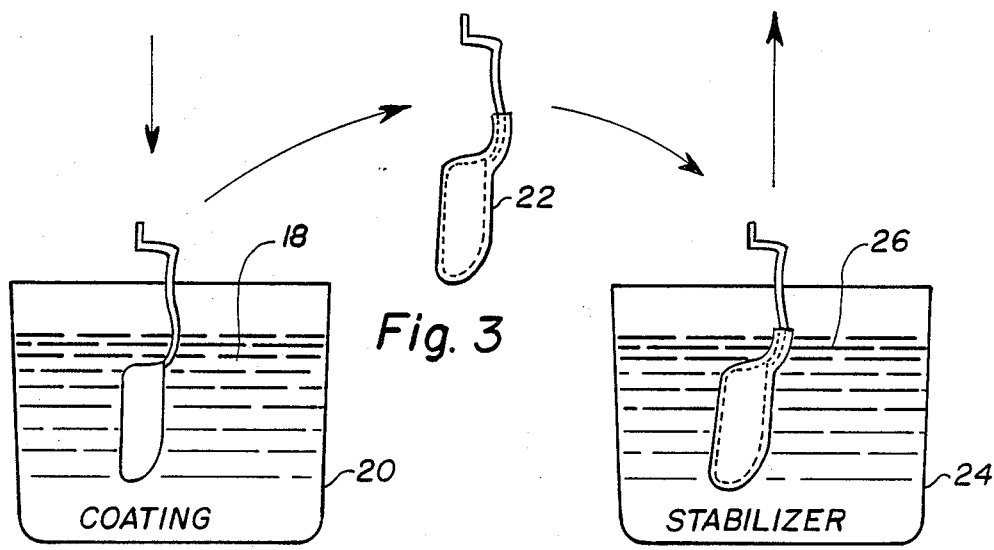
FIG. 2 is a diagrammatic view showing a coating bath in which the loaded impression tray is immersed for coating therewith.
FIG. 3 is an exemplary side view of a loaded and coated tray in transit from said coating bath.
FIG. 4 is a diagrammatic view showing a stabilizing bath in which the loaded and coated tray has been immersed to convert the coating material to a stable sheet-like skin on the loaded tray.

Referring to the drawings and especially FIG. 1, relating to an embodiment where a dental impression tray is used to contain flowable dental impression material, a suitable impression tray 10 is shown which is of a conventional shape, in the form of a "U" and having a handle 12 extending from the mid portion thereof to permit manipulating the tray in a conventional manner. Although handle 12 is illustrated as being in the mid portion, it will be apparent to those skilled in the art that the handle may be positioned wherever convenient to handle the particular type of dental tray used in the invention.

Figure 5:
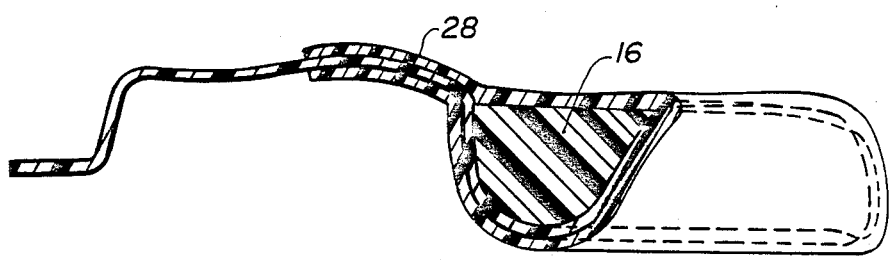
FIG. 5 is an enlarged sectional view of a loaded and coated tray as seen on the line 5—5 of FIG. 1.

In addition to prepackaged upper and lower full arch trays, as illustrated in FIG. 5, prepackaged upper and lower quadrant trays, anterior trays, three function trays and counter impression trays may be provided in accordance with the present invention A three function tray is one in which a frame is provided for containing impression materials laterally, and gauze or a similar material is used for holding the impression materials vertically, said tray being adapted to provide an impression of upper and lower teeth simultaneously, and also to obtain a registration of the relationship between the upper and lower teeth.

In an alternative embodiment, impression material alone may be provided in a shape suitable for obtaining a dental impression and prepackaged using means to contain the impression material, said means being a package material or skin whereby the impression material is preshaped, and maintains the shape of the skin, or is easily molded together with the skin into the shape needed to obtain an impression.

By skin, as used herein, it is meant that a covering is provided over the dental impression material, that at least in part directly restrains the flow of the impression material and preferably is so tight as to substantially reduce or eliminate the possibility of air from being trapped between said dental impression material and said covering. In the preferred embodiment, the skin will be a different kind of material from that of the impression material. The skin material of the illustrated embodiment will have properties such that the skin will be capable of maintaining the shape of the flowable dental impression material in a configuration usable for taking a dental impression when shaped mechanically and will hold the impression material in its intended shape for a sufficient time to permit its use. This shape maintenance will restrain the impression materials natural or inherent flow. In a preferred embodiment, the skin material will be flexible and deformable but substantially non-stretchable material under the conditions in which it is used, namely in retaining the inherent flow forces of the impression material. In an alternative embodiment, the skin material will be a rigid but easily perforated material which may be suitable for stripping from the impression material immediately prior to use. Among the preferred materials used for said skin are waxes, thermosetting materials, plastics, elastomers and film forming materials. Examples of such materials are natural latex, which is most preferred, polyvinyl alcohol, polyvinyl pyrrolidone, shrink wrap and PARA-FILM ®(American Can). The skin may be applied by any convenient method, such as by spraying (e.g. polyvinyl alcohol) or dipping in a liquid bath (e.g. natural latex).

Referring to FIG. 1, the U-shaped portion 14 of the tray is pre-loaded with suitable impression material of the type desired to be used in accordance with the present invention. Preferably, the material is of the type that has low flowability, and by way of example, the viscosity thereof preferably is of the order of about one million centipoises. For example, impression materials of the type subject to curing by application of actinic light are of a special utility. However, the invention is broadly applicable to one component systems and certain specific examples are set forth hereinafter.

Referring to FIG. 1, exemplary material 16 is filled to a desired degree into the portion 14 of the tray in any suitable manner and by any appropriate means, manual or otherwise. Prior to introducing the impression material, however, and in accordance with a preferred embodiment of the invention, the tray portion 14 is first coated on the interior with an appropriate cement or adhesive for the purpose of insuring retention of a cured impression within the tray when the cured impression is removed from the dental anatomy. One appropriate cement or adhesive which has been found to be highly satisfactory is a urethane modified bis GMA resin in a solvent blend of nitromethane and methylonechloride containing a photo initiator and a photo accelerator. Other appropriate cements may be available and used.

As indicated hereinabove, it is preferred that the impression materials 16 be of the type that is readily flowable, ere capable of recording relatively minute details of dental anatomy to a greater extent than is possible with the more viscous materials previously used. In view of the fact that the ends of the U-shaped portion 14 of the tray 10 are open, it can be appreciated that the more flowable impression material can run from the ends of the tray, and the present invention provides means to prevent this. However, it can be appreciated that the more flowable the impression material happens to be, the more difficult will be the enclosing of the same in the impression tray and packaging it so as to be leak-proof.

In the preferred embodiment flowable impression material is encapsulated or enclosed within U-shaped portion 14 of the tray, and to accomplish this it has been found that natural latex is a highly appropriate skin material which can be employed to cover the entire tray and its contents. Accordingly, the present invention provides that the tray 10, after loading with the impression material 16, is quickly immersed in a coating solution 18 of natural latex contained in a suitable reservoir 20, and is maintained in the solution a short period of time, sufficient to completely cover the tray and the impression material, preferably about 5 seconds. Such immersing can be accomplished either manually or automatically by suitable equipment, not shown.

Immediately following the immersion step, and withdrawal of the coated tray product 22 from the latex, it is immersed in a bath 24 of stabilizer solution 26. One highly suitable form of such solution has been found to be a solution of acetic acid, such as a 5% solution, which quickly and readily stabilizes natural latex into a continuous coating 28 which encloses the tray and contained impression material 16 in a manner which is highly suitable to constitute a package. If it is found that the single coating is inadequate, the foregoing procedure may be repeated one or more times until a coating of required and desired thickness is obtained.

Another advantage of using natural latex is that it is light-transmittable to a sufficient degree that it is capable of transmitting actinic light therethrough to the contour of a dental anatomy of which an impression is being made and, while remaining upon the anatomy, the molded impression may be cured by the application of actinic light or the like to which the tray is exposed for a sufficient period of time to effect desired stabilizing and curing of the impression. Preferably the actinic light used will be in the visible range, and most preferably will be about 450 nm to about 520 m.

When it is desired that an impression of dental anatomy be made in the material 16 per se, this may be done by quickly stripping the latex coating 28 from the tray and the material therein and then applying the tray directly to the portion of the dental anatomy of which an impression is desired. Under such circumstances, it is apparent that relatively small details of the dental anatomy may be recorded in the material while the same is being cured such as by the application of actinic light thereto while the tray and specifically the material are maintained in contact with the portion of the anatomy of interest. An impression material used in such a method must have a sufficiently high viscosity such that it will not run out of the tray in the few minutes that are required to take the dental impression and cure the material. In the stripping step the practitioner may cut the skin with a knife or scalpal before it is stripped, or the skin may be processed in the factory to provide for easy tearing.

As an alternative embodiment of the present invention, the skin provided over the dental tray can be made to have properties such that the practitioner can obtain a crude approximation or first impression of the tissues by taking an impression through the skin. When the first impression has been taken, and the film covering the tray has been removed, a second application of visible light cured impression material can be placed into the void created by removal of the film, such as by means of a spatula, and the impression material can be applied to the teeth as for example with a syringe, and a second, more precise impression can then be obtained. Since the impression material is contained in this method, the impression material may be less viscous than those used when the skin is stripped off before the impression is taken.

When the impression is taken through the skin, the skin acts as a spacer, and its removal provides more room to apply the secondary or light body impression material which is used to obtain the second impression. The light body impression material preferably is provided having a viscosity much lower than the tray material so that an impression having minute detail can be obtained. Such low viscosity material also can be easily applied using the syringe.

In the embodiment in which a flowable skin material is used, such as parafilm or latex, which distorts and flows into the impression when first impression is made, geometrically accurate duplication of the dental anatomy with regard to angles is achieved since the skin material does not resist the taking of the impression. When the skin is stripped from the dental impression material, and the space occupied by the skin is filled with secondary or light body impression material, the secondary impression material is required only to record minute details of the dental anatomy, and is not required to provide additional bulk in the impression as is required by the prior art method which used a spacer to obtain only a rough estimation of the dental anatomy since the spacer used in the prior art resists the impression and stretches and said resistance causes additional volume to be added to the first impression.

In an alternative embodiment, the dental impression material may be provided in a shape which is suitable for obtaining a dental impression and contained in a skin as described above. For example, the dental impression material may be rolled into a cylinder, the cylinder bent in the shape of a "U" of a size suitable for fitting into the mouth to obtain a dental impression, and the "U" shaped dental impression material may be dipped into latex as described above. Preferably such a material will be packaged to retain its shape until it is used, but it is important only that the skin provided retain the dental impression material in the general shape and size required to obtain a dental impression. Minor reshaping of the dental impression material and the skin can be provided by the practitioner prior to use. In an alternative embodiment, the practitioner may bend a linear cylinder of impression material into a general U-shape. A linear cylinder of such material may be more suitable for storage If it is desired to firmly retain the shape of the dental impression material, a tough but flexible and deformable skin will be required, such as may be provided by shrink wrap or similar plastic tubing.

In the case where a three function tray is used, stiffer dental impression materials are required in order to limit sagging since such trays do not have a containing surface inside the frame. However, such materials must not be so stiff that they do not readily deform and thereby cause distortion of the frame, which ultimately may cause an inaccurate duplication of the dental anatomy. An impression material that possesses a strain value of no more than about 1½% to about 2½% as measured by ADA Spec. #19 is preferred.

Examples of the preparation of a polymerizable impression materials suitable for use in the preferred embodiment of the invention follow:

EXAMPLE 1

A preferred elastomeric prepolymer oligomer compound was prepared according to the following formulation:

| | |
|---|---|
| Polypropylene glycol MW-2,000 Voranol 2120 (Dow Chemical) | 690 g |

-continued

| Trimethyl hexamethylene diisocyanate (Thorson) | 145 g |
| Dibutyl tin dilaureate | 0.4170 g |
| Hydroxyethylmethacrylate (HEMA) (Esschem) | 50.0 g |
| 1,4 Butane diol (BASF) | 31.0 g |
| Isocyanatoethyl methacrylate (Dow Chemical) | 53.4 g |

The procedure was as follows:

One mole of polypropylene glycol (2 equivalents of hydroxy) are reacted with two moles of trimethyl hexamethylene diisocyanate (4 equivalents of isocyanate) employing the dibutyl tin dileureate.

The polypropylene glycol was dewatered with molecular sieve (4A) for two days. Then it was charged into a 2 liter reactor. Stirring and are air flow through the reactor was begun. The dibutyl tin dilaureate was added to the glycol dropwise and allowed to stir in. Then the trimethyl hexamethylene diisocyanate was added to the glycol-catalyst mixture dropwise using a separatory funnel. The addition was done at room temperature and the drop rate was controlled to keep the temperature below 50C. After about three hours, all the diisocyanate had been added. The mixture was allowed to stir overnight with a heating mantle up around the reactor (no heat turned on). The next day 45 grams HEMA was added dropwise, again controlling the drop rate to keep the pot temperature below 50C. After all the HEMA was added, the 1,4 Butane diol was added dropwise to the reactor contents. This mixture was allowed to stir overnight. The next day, isocynatoethyl methacrylate was added dropwise through the separatory funnel and stirred in. A slight excess of HEMA (5 grams) was finally added to the pot about three hours after the final addition of isocyanatoethyl methacrylate to be sure all the free isocyanate was reacted. The pot contents were allowed to stir for 24 hours and then unloaded.

EXAMPLE 2

A dental impression forming composition suitable for use as a tray material was compounded by hand mixing the following formulation at ambient conditions.

| Resin of EXAMPLE 1 | 100 parts by wt. |
| Camphoroquinone | 0.15 " |
| Methyl diethanol amine (MDEA) | 0.5 " |

The dental impression forming composition was then tested for its relevant characteristics with the following results:

The composition was irradiated with a 500 watt General Electric Photo-EBv photoflood lamp containing light from the visible light spectrum for 5 minutes with the lamp approximately 2 inches from the dental impression forming composition specimen. The material cured to an elastic solid. The following testing results were obtained using ADA Spec 19 (1984) for non-aqueous elastomeric impression materials when the cured dental impression composition cured by irradiation as described was tested:

| Compression Set (%) | Strain (%) | Dimensional Change (%) |
|---|---|---|
| 0.65 | 3.75 | 24 hrs 0.23 expansion |
|  |  | 1 wk 0.27 expansion |

EXAMPLE 3

An elastomer prepolymer oligomer compound suitable for use as a tray material in this invention was prepared according to the following formulation:

| Polypropylene glycol (MW 4000) Voranol 2140 (Dow Chemical) | 834.6 g |
| Trimethylhexamethylene diisocyanate (Thorson Chemicals) | 87.7 g |
| Stannous octoate | 0.50 g |
| Hydroxyethyl methacrylate (Rohm & Haas) | 27.1 g |
| 1,4 Butanediol (BASF) | 18.7 g |
| Isocyanatoethyl methacrylate | 30.8 g |

The procedure was as follows:

In theory, one mole of polypropylene glycol (2 equivalents of hydroxy) are reacted with two moles of trimethylhexamethylene diisocyanate (4 equivalents of isocyanate) employing the stannous octoate as catalyst.

The polypropylene glycol was charged into a 2 liter reacter. Stirring and dry air flow through the reactor was begun. The stannous octoate was charged to the reactor and allowed to stir in. Then the trimethylhexamethylene diisocyanate was added to the glycol catalyst mixture dropwise using a separatory funnel. The addition was done at room temperature and was controlled to keep the temperature below 50° C. Addition was complete after 30 minutes. The contents were allowed to stir for 30 minutes more. Samples were taken and titration was done to determine isocyanate content. Isocyanate was found to be 1.9% which indicated complete reaction of the polypropylene glycol and trimethyhexamethylene diisocyanate. Then the 27.1 grams of HEMA were added all at once to the reactor contents which were at a temperature of about 40° C. The contents were allowed to stir for 45 minutes. Then titration samples were taken and the isocyanate content determined to be 0.95%. This indicated complete reaction of the HEMA with the isocyanate terminated prepolymer leaving 1 equivalent of isocyanate sites for reaction with 1,4 butane diol. At this point 18.7 grams of 1,4 butane diol were added to reactor contents all at once and allowed to stir in for 2 hours. The temperature of the reactor continued between 4° and 50° C. for this procedure. At the end of 2 hours the isocyanatoethyl methacrylate was added dropwise to the reactor using a separatory funnel. This addition took approximately 30 minutes. Stirring was continuous until the next morning to be sure all the free isocyanate was reacted. Then the pot contents were unloaded.

EXAMPLE 4

A dental impression forming composition suitable for use a tray material was compounded by hand mixing the following formulation at ambient conditions:

| Resin of EXAMPLE 3 | 39.0 g |
| Di (C$_{7-9-11}$ Alkyl) Phthalate (Palatinol 711 P from BASF) | 1.60 g |
| Peppermint Oil | 0.20 g |
| Titanium IV neoalkoxy, tris (dodecylbenzene) sulfanato (Ken React LICA 09 from Kenrich Petrochemicals, Inc.) | 0.20 g |
| fumed silica (Aerosil R-972 from Degussa) | 4.20 g |
| blue pigment (Dayglo) | 0.080 g |
| Feldspar | 35.5 g |
| Camphorquinone | 0.10 g |

| | |
|---|---|
| 4 Dimethylaminobenzonitrile | 0.24 g |

The composition was irradiated for 1 minute using the photoflood lamp procedure of Example 2. The material cured to a elastic solid.

A sample of material 20 mm thick was covered with a sheet of clear Mylar about 1 mil thick. The sheet was in direct contact with the sample. The light was directly engaged against the sheet of Mylar. The light was on 10 seconds. Curing was to a depth of 8 mm as determined by wiping away the uncured material from the bottom of the sample and measuring the remaining cured material.

EXAMPLE 5

A dental impression forming compound suitable for use as a light body impression material according to the invention was compounded by a double planetary mixer at reduced pressure:

| | |
|---|---|
| Resin of EXAMPLE 3 | 45.98 g |
| Camphorquinone | 0.09 g |
| 4-Dimethylaminobenzonitrile | 0.4 g |
| Butylated Hydroxy Toluene | 0.05 g |
| Di ($C_{7-9-11}$ Alkyl) Phthalate (Palatinol 711 P from BASF) | 2.0 g |
| Titanium IV neoalkoxy, tris (dodecylbenzene) sulfanato (as in Example 4) | 0.25 g |
| Fused Quartz | 43.6 g |
| fumed silica (as in Example 4) | 7.6 g |
| blue pigment (Dayglo) | 0.25 g |

The composition was irradiated for 40 seconds using the photoflood lamp procedure of Example 2. The material cured to a rubbery solid.

The depth of cure test procedure of Example 4 was performed and the depth of cure was 13 to 14 mm.

The material gave the following physical properties as tested by ADA Spec. #19 referred to in Example 2:

| Compression Set | Strain | Dimensional Change | Detail Reproduction | Flow |
|---|---|---|---|---|
| 1% | 2.6% | 0.05% | 20 micron line | 0.10% |

A polymer for use as a tray impression material of the invention was prepared according to the following formulation:

| | |
|---|---|
| Resin of EXAMPLE 3 | 390.41 g |
| Camphorquinone | 0.79 g |
| Butylated Hydroxy Toluene | 0.170 g |
| 4-Dimethylaminobenzonitrits | 3.63 g |
| Fused Quartz | 437.3 g |
| Magenta Pigment (Dayglo) | 0.80 g |
| Fumed silica | 139.9 g |
| Gamma-Methacryloxypropyltrimethoxysilane | 5.00 g |
| Di ($C_{7-9-11}$ Alkyl) Phthalate | 19.50 g |
| Titanium IV neoalkoxy, tris (dodecylbenzene) sulfonato | 2.50 g |

The composition was tested for depth of cure using the procedure of Example 6 and gave results of 19–20 mm. The composition was irradiated for 40 seconds with a Prismetics lite using the wide tip with the tip directly above the dental impression forming composition specimen using a Mylar spacer. The material cured to a rubbery solid and gave the following physical properties as tested by ADA spec. #19:

| Compression Set | Strain | Dimensional Change | Detail Reproduction |
|---|---|---|---|
| 0.60% | 1.1% | 0.02% | 20 micron line |

EXAMPLE 7

An adhesive for use in the invention, which is painted on the dental trays before the trays are filled with VLC Impression Material and dipped in latex, is prepared according to the following example:

Adhesive Preparation

Preparation of BIM (the reaction product of Bis-GMA and IEM, needed for the preparation TNCO, the reaction product of Bis-GMA and TMDI). The following ingredients were used:

626.0 g (1.218 moles) of 2,2-Bis[4-3 (3-methacryloxy-2-hydroxypropoxy-phenyl]-propane (Bis-GMA)

234.4 g (0.808 moles) of triethyleneglycol dimethacrylate (TEGDMA)

234.4 g (0.923 moles) of 1,6 Hexanediol dimethacrylate (HMDMA)

321.5 g (2.074 moles) of Isocyanatoethyl methacrylate (IEM)

1.40 g (0.003 moles) of Stannous Ocotate (T-9)

1.12 g (0.0051 moles) of Butylated Hydroxy Toluene (BHT)

The Bis-GMA was weighed into a dry 2 liter reactor. The TEGDMA and HMDMA were added to the Bis-GMA. Stirring and dry air flow through the reactor was begun and the mixture was stirred for 30 minutes until it was homogenous. Then the stannous octoate was added dropwise and stirred in for 15 minutes. The IEM was weighed into a beaker and poured into a 500 ml. addition funnel where it was added dropwise to the reactor. The addition was done at a speed to keep the reactor temperature below 50° C. Addition took approximately 3½ hours. It was allowed to stir overnight. The next morning a sample was taken, found to be free of residual IEM, and was unloaded from the reactor.

Preparation of TNCO

The following materials were used:
541.5 g (1.05 moles) of 2,2-Bis[4-3(3-methacryloxy-2-hydroxypropoxy)-phenyl]propane (Bis-GMA)
541.5 g (0.848 moles) of BIM resin
111.8 g (0.386 moles) of TEGDMA
111.8 g (0.440 moles) of HMDMA
190.4 g (0.907 moles) of Trimethylhexamethylene Diisocyanate (TMDI)
2.25 g (0.0048 moles) of T-9
1.20 g (0.0055 moles) of BHT The Bis-GMA and BIM were weighed into a dry 2 liter reactor. TEGDMA and HMDMA are then weighed into the reactor. Stirring and dry air flow through the reactor were begun. The reactor contents were stirred for 30 minutes until a homogeneous mixture resulted. The T-9 was then added to the reactor dropwise and mixed in 15 minutes. Then the TMDI was weighed into a beaker and poured into a 250 ml. addition funnel where it was added dropwise. Addition was done at a speed to keep the temperature below 50° C. Addition was complete in approximately 1½ hours. The resin was stirred for 36 hours maintaining the temperature between 45°-53° C. Then a sample was taken, found to be free of residual TMDI, and the reactor was unloaded.

Initiation of TNCO Resin

The TNCO resin was initiated for a visible light curing system as outlined below:

| TNCO resin | 99.24% |
|---|---|
| Camphorquinone | 0.15% |
| 4-Dimethylaminobenzonitrile | 0.61% |

Procedurally, the TNCO resin was weighed into a glass jar. The camphorquinone and 4-dimethylaminobenzonitrile were weighed out separately and added to the TNCO. This mixture was heated to 50° C. using a water bath and then stirred for 30-45 minutes until it was homogenous.

Preparation of Adhesive

The following ingredients were used:

| Iniated TNCO resin | 56.71% |
|---|---|
| Methylene Chloride | 23.81% |
| Nitromethane | 19.48% |

Procedure:

The warm initiated TNCO resin was weighed into a beaker. The nitromethane and methylene chloride were weighed into a glass jar and stirred for 2-3 minutes. Then the warmed TNCO resin was slowly poured into the methylene chloride/nitromethane mixture with stirring. The mixture was stirred after addition was complete for 20 minutes.

The present invention provides ready means for encapsulating an impression tray which is pre-filled with flowable dental impression material but which is incapable of flowing therefrom until ready for use in view of the durable and flexible skin which completely covers and encapsulates the loaded tray. As indicated, curing may be done in conventional ways or, as is preferred, actinic light may be applied to a transparent tray and the light-curable impression material preferably contained therein and enclosed in an overall manner by the preferred coating of natural latex or its equivalent.

As an alternative to providing a clear dental tray, through which visible light can be transmitted to cure the impression material, in order to protect the impression material from premature polymerization, the tray may be made of a material that blocks outside light, but is provided with a means for piping visible light into the impression material, such as is described by Wang in U.S. Pat. No. 4,553,936, assigned to Dentsply International.

As will be apparent to those skilled in the art, in certain applications it also may be desirable to pipe visible light into a transparent dental tray.

The foregoing description illustrates preferred embodiments of the invention However, concepts employed may, based upon such description, be employed in other embodiments without departing from the scope of the invention. Accordingly, the following claims are intended to protect the invention broadly, as well as in the specific forms shown herein.

We claim:

1. A process for prepackaging a flowable light curable dental impression material which is in a form suitable for making a dental impression comprising the steps of:
   (a) predisposing said dental impression material in a manner suitable for obtaining a dental impression and;
   (b) retaining at least a portion of said dental impression material by encasing said dental impression material in a skin, said skin having strength and stretch resistance suitable for retaining said dental impression material and permitting a dental impression to be taken through said skin.

2. The process according to claim 1 which comprises the step of forming said skin from material that is flexible, deformable, and non-stretchable under the conditions of use.

3. The process according to claim 1 which comprises the step of forming said skin from a material that is rigid, and easily punctured.

4. The process according to claim 1 comprising the step of making said skin from wax, plastic, thermoplastic material, elastomeric material or film forming material.

5. The process according to claim 1 comprising the step of making said skin from a material selected from the group comprising shrink wrap, latex, plastic, polyvinyl alcohol, polyvinyl pyrrolidone, and parafilm, and providing said skin in a substantially continuous layer.

6. The process according to claim 1 which comprises the step of disposing said dental impression material in a cylindrical shape and providing a skin made of shrink wrap.

7. A prepackaged dental impression means comprising, a light curable flowable dental impression material in a form suitable for taking a dental impression, and skin covering at least a portion of the surface of said flowable dental impression material.

8. A prepackaged dental impression means of claim 7 in which said skin comprises a flexible, deformable, and substantially non-stretchable material under the conditions of use.

9. The prepackaged dental impression means of claim 7 in which the skin is a rigid, easily punctured material.

10. The prepackaged dental impression material according to claim 7 in which said skin comprises a layer of material selected from the group comprising shrink wrap, latex, polyvinyl alcohol, pyrrolidone, and parafilm.

11. The prepackaged dental impression means of claim 7 in which said dental impression material has a U-shaped cylindrical shape and said skin comprises shrink wrap.

12. The dental impression package of claim 7 in which said skin is distortable and flowable and when an impression of the dental anatomy is taken, said skin flows into said impression without resistance and forms a geometrically accurate first dental impression.

13. The packaged dental impression means according to claim 8 in which at least a part of said package comprises a dental tray.

14. The prepackaged dental impression means according to claim 13 in which said dental tray has a coating of adhesive cement applied thereto prior to the loading of impression material thereinto, whereby when an impression of dental anatomy has been made in said impression material and cured therein to stabilize the impression, said cement will retain said impressed impression material when removing said impression material from the dental anatomy.

15. The prepackaged dental impression means according to claim 14 in which said adhesive cement comprises urethane modified Bis-GMA resin in a solvent blend of nitromethane and methylenechloride containing a photo initiator and photo accelerator.

16. The prepackaged dental impression means according to claim 13 in which said skin is removable when an impression is to be made, whereby the dental anatomy of which an impression is to be made can be pressed directly into the exposed impression material.

17. The prepackaged dental impression means according to claim 13 in which said skin is light-transmitable.

18. The prepackaged dental impression means according to claim 13 which is made of a material which is transparent to visible light and said impression material is a light cured impression material, such that the impression material can be cured by shining light on said dental tray while said impression material is in contact with the anatomy.

19. The prepackaged dental impression means according to claim 13 which is provided with a means for piping light through said tray into the dental impression material.

20. A method of affixing a dental impression material to a dental tray and simultaneously setting said impression material comprising the steps of sequentially
 (a) coating a light transparent dental tray with a light activated adhesive
 (b) loading said dental tray with light activated impression material
 (c) obtaining an impression of the dental anatomy
 (d) applying actinic light simultaneously to said adhesive and said impression material and curing said adhesive and said impression material.

21. The method of claim 20 in which said adhesive comprises urethane modified Bis-GMA resin in a solvent blend of nitromethane and methylene chloride and containing a photoinitiator and photoaccelerator.

* * * * *